United States Patent [19]

Perchonock

[11] 4,140,688

[45] Feb. 20, 1979

[54] TRICYCLIC (AZETO-ISOQUINOLINE) β-LACTAMS

[75] Inventor: Carl D. Perchonock, Philadelphia, Pa.

[73] Assignee: SmithKline Corporation, Philadephia, Pa.

[21] Appl. No.: 892,531

[22] Filed: Apr. 3, 1978

[51] Int. Cl.$^2$ ............................................. C07D 451/02
[52] U.S. Cl. .............................. 546/94; 260/340.9 R; 260/239 A; 424/258
[58] Field of Search ................................. 260/287 CF

[56] References Cited

PUBLICATIONS

Huffman et al., JACS, 99, 2353, Oct. 1976.

*Primary Examiner*—Donald G. Daus
*Assistant Examiner*—David E. Wheeler
*Attorney, Agent, or Firm*—Stuart R. Suter; Alan D. Lourie; William H. Edgerton

[57] ABSTRACT

A new compound with a nucleus containing a benzo-fused carbocyclic β-lactam system is disclosed. The compound has antibacterial activity against *B. subtilis*.

5 Claims, No Drawings

TRICYCLIC (AZETO-ISOQUINOLINE) β-LACTAMS

Research in the β-lactam field has centered mainly on penicillins and cephalosporin compounds, both of which have the β-lactam fused in a bicyclic ring system. Recently, new β-lactam systems which maintain their antibiotic properties have been reported. Examples include nocardicin [J. Amer. Chem. Soc., 98, 3023 (1976)], which contains a monocyclic β-lactam nucleus, clavulanic acid (Belgian Pat. No. 827,926), which has an oxygen-containing bicyclic β-lactam nucleus, and bicyclic systems related to cephalosporins in which the sulfur atom has been moved to another position, [J. Amer. Chem. Soc., 99, 2353 (1977)] or has been replaced by oxygen or a methylene group [J. Med. Chem., 20, 551 (1977)]. The carbocyclic cephalosporin system noted above is believed to be the closest prior art; however it is also believed not to be material to the patentability of the compounds of this invention. Other similar β-lactams systems have been reported; however, all these systems are also not believed material prior art to the present invention.

I have now prepared a novel tricyclic β-lactam system which contains a fused benzo system; in particular, derivatives of the 1α-amino-1,2-dihydro-2-oxo-9bβH-azeto[2,1-a]isoquinoline-4-carboxylic acid nucleus.

DESCRIPTION OF THE INVENTION

The compounds of this invention have the following chemical formula

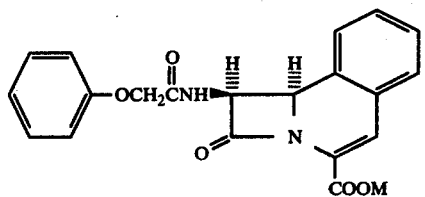

wherein

M is hydrogen, a carboxylic acid protective ester residue, or a pharmaceutically acceptable non-toxic cation.

The term "a carboxylic acid protective ester group" is one which has a clear and definite meaning within the art. Many ester groups are known and used in the art to protect a carboxylic acid group from interfering with chemical reactions in undesired ways. At the appropriate time, the esters are cleaved by standard methods to give the desired free carboxylic acid moiety. Many examples of such ester groups are set forth in the chemical literature, including review articles and books such as "Protective Groups in Organic Chemistry", McOmie ed., Plenum Press, New York, 1973. Examples of the most common esters include t-butyl, benzyl, nitrobenzyl, methoxybenzyl, benzhydryl, and trichloroethyl. The selection of which ester group to use depends on various factors, including subsequent reaction conditions and desired methods of removal. The selection of the proper ester group is within the ability of persons skilled in the art.

Pharmaceutically acceptable non-toxic cations are also well-known in the art. In general, they include alkali metal cations, alkaline earth cations and organic or inorganic ammonium cations. The sodium and potassium salts are particularly advantageous. Again, the selection of useful and proper cations is within the ability of persons skilled in the art.

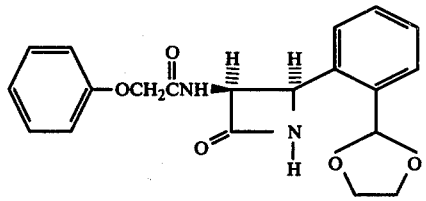

1

The compounds of this invention are prepared by a totally synthetic route with the monocyclic β-lactam (1) as starting material. Compound 1 is prepared by the sequence of reactions set forth in Scheme I. Conversion of β-lactam 1 into the compounds of this invention is outlined in Scheme II.

SCHEME I

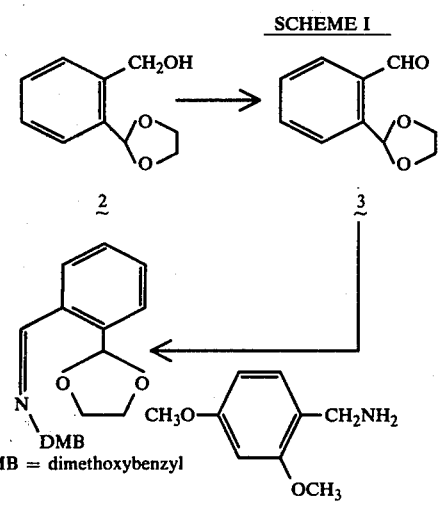

DMB = dimethoxybenzyl

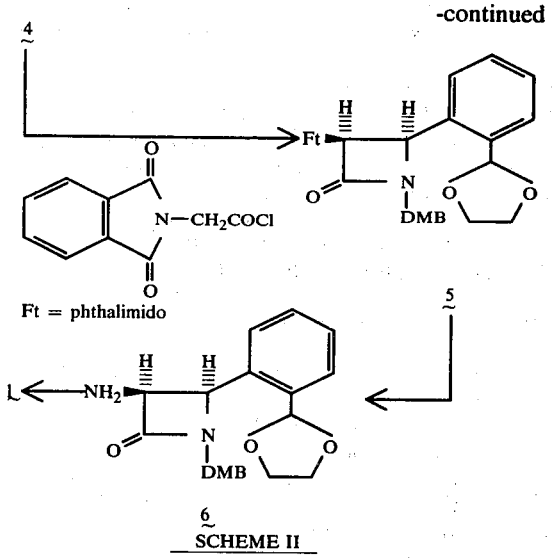

Ft = phthalimido

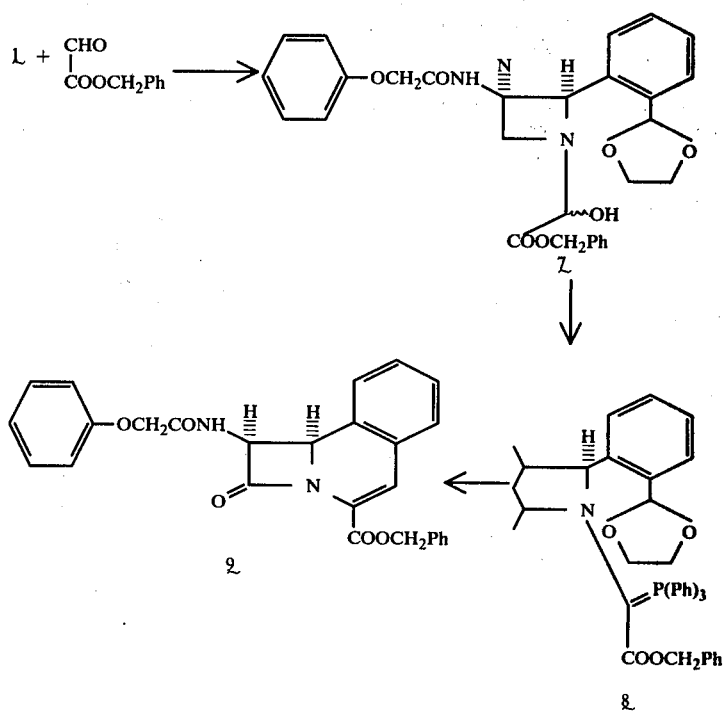

SCHEME II

Benzyl alcohol 2 [J. Chem. Soc.(C), 1818 (1969)] is oxidized by standard oxidizing agents such as CrO₃ to benzaldehyde 3. Condensation of 3 with 2,4-dimethoxybenzylamine gives imine 4, which is reacted directly with phthalimidoacetyl chloride to give monocyclic β-lactam 5 wherein Ft is phthalimido. Treatment of 5 with methylhydrazine gives the amino-β-lactam derivative 6. Acylation of 6 with phenoxyacetyl chloride by standard methods followed by oxidative cleavage of the dimethoxybenzyl group with $K_2S_2O_8$ gives the monocyclic β-lactam 1.

When β-lactam 1 is treated with an ester of glyoxylic acid (where the ester is selected from those protective esters known within the art) in the presence of triethylamine, compound 7 is obtained. The alcohol moiety of 7 is converted to the chloro derivative by treatment with thionyl chloride and pyridine. Reaction of the chloro derivative with triphenyl phosphine gives the ylide 8. Treatment of 8 with a mild acid such as p-toluenesulfonic acid yields the ester compounds of this invention. Cleavage of the ester group by standard methods gives the compounds of the invention where M is hydrogen. The free acids can be converted to the pharmaceutically acceptable salts by standard methods known in the art.

The compounds of this invention where M is hydrogen or a cation have antibacterial activity against *B. subtilis*. They are useful for sterilization of laboratory glassware or for treating infections of *B. subtilis* in animals.

The compounds of this invention where M is a protective ester group are useful as intermediates for the antibacterially active compounds.

The following examples are presented to illustrate general methods of preparing the compounds of this invention to one skilled in the art and are not to be construed as limiting the scope thereof. All temperatures are given in degrees Centigrade.

EXAMPLE 1

2-(2-Dioxolanyl)benzaldehyde

A suspension of sodium acetate (6.56 g, 0.08 mol) and pyridinium chlorochromate (17.2 g, 0.08 mol) in dry methylene chloride (200 ml) was cooled in an ice bath under a nitrogen atmosphere and treated with a solution of 2-(2-dioxolanyl)benzyl alcohol (9.6 g, 0.053 mol) in methylene chloride (25 ml) over a 15 minute period. The reaction was stirred at room temperature for 2 hours and diluted with ether (200 ml). The solid was collected and washed with ether, and the filtrate was washed with 5% NaHCO$_3$ and brine and dried. The solution was evaporated to give the title aldehyde; 7.8 g (82%).

EXAMPLE 2 cis-1-(2,4-Dimethoxybenzyl)-2-[2-(2-dioxolanyl)-phenyl]-4-oxo-3-phthalimidoazetidine To an ice-cold solution of 2,4-dimethoxybenzylamine (3.6 g, 21.5 mmol) in methylene chloride (40 ml) was added a solution of aldehyde from Example 1 (5.0 g, 22.4 mmol) in methylene chloride (25 ml). The solution was stirred 10 minutes, 4A molecular sieves (9 g) were added, and the reaction was stirred at room temperature for 1.75 hours. IR analysis indicated no amine or aldehyde groups.

The mixture was cooled in ice and triethylamine (2.61 g, 25.8 mmol) was added, followed by the dropwise addition of phthalimidoacetyl chloride (5.54 g, 24.8 mmol) in methylene chloride (40 ml) over a 15 minute period. The reaction was stirred for 30 minutes and then filtered. The filtrate was washed with 5% NaHCO$_3$ and brine, and the organic phase ws dried and evaporated to an oil, which on standing with ether and chloroform gave a solid product; 9.3 g. The solid was recrystallized from ethyl acetate; 7.1 g (64%), mp 170–172°.

EXAMPLE 3 cis-3-Amino-1-(2,4-dimethoxybenzyl)-2-[2-(2-dioxolanyl)-phenyl]-4-oxoazetidine

The product from Example 2 (5.8 g) was dissolved in methylene chloride (40 ml) and filtered to remove a trace of insoluble solids (0.15 g). The filtrate was cooled with an ice bath and treated under a nitrogen atmosphere with methylhydrazine (0.85 g, 18.7 mmol). The reaction was stirred 2 days under nitrogen at room temperature and then filtered to remove a solid, which was washed with a small amount of methylene chloride. The filtrate was evaporated in vacuo to give 4.65 g of the title product.

EXAMPLE 4 cis-1-(2,4-Dimethoxybenzyl)-2-[2-(2-dioxolanyl)-phenyl]-4-oxo-3-phenoxyacetylaminoazetidine The amino compound from Example 3 (4.22 g, 11 mmol) was dissolved in ethyl acetate (60 ml) and cooled in an ice-alcohol bath. Triethylamine (1.67 g, 16.5 mmol) was added, followed by the dropwise addition of phenoxyacetyl chloride (2.06 g, 12.1 mmol) over a period of 5 minutes. The reaction was stirred for 45 minutes with cooling and then filtered. The filtrate was washed with 5% NaHCO$_3$ and brine. The dried filtrate was evaporated to give the title product; 2.0 g. The product was recrystallized from ethyl acetate-ether; 1.02 g, mp 137–138°. The solid which was filtered from the reaction solution was stirred with hot ethyl acetate (100 ml) and filtered. The filtrate was treated with ether (200 ml) and cooled to give additional product; 3.91 g, mp 138–139°.

EXAMPLE 5 cis-2-[2-(2-Dioxolanyl)phenyl]-4-oxo-3-phenoxyacetylaminoazetidine

The product of Example 4 (1.56 g, 3 mmol) was dissolved in a mixture of acetonitrile (120 ml) and distilled water (30 ml), degassed with argon for 30 minutes, and brought to reflux. A degassed solution of K$_2$S$_2$O$_8$ (5.67 g, 21 mmol) and Na$_2$HPO$_4$.7H$_2$O (2.81 g, 10.5 mmol) in distilled water (120 ml) was added in 8 equal portions at 4 minute intervals to the refluxing solution, the reaction being kept at pH >6 by the addition of solid Na$_2$HPO$_4$.7H$_2$O. The acetonitrile was evaporated and the residue was extracted with ethyl acetate. The extracts were washed with brine, dried, and evaporated to an oil, 2.07 g. The oil was extracted with petroleum ether to remove the dimethoxybenzaldehyde and then was triturated with ethyl acetate-ether. It was cooled in ice and the resulting solid product was collected; 0.54 g (49%), mp 137–138° dec.

EXAMPLE 6

Benzyl α-Hydroxy-α-[cis-2-[2-(2-dioxolanyl)phenyl]-4-oxo-3-phenoxyacetylamino-1-azetidinyl]acetate Freshly distilled benzyl glyoxylate (312 mg, 1.9 mmol) and freshly distilled tetrahydrofuran (15 ml) were stirred with 4A molecular sieves for one hour and then cooled in ice. To this solution was added the solid product from Example 5 (437 mg, 1.19 mmol) followed by the dropwise addition of triethylamine (240 mg, 2.37 mmol). The ice bath was removed and the reaction was stirred for 1.5 hours. The solution was filtered and the filtrate was evaporated to dryness. The residue was dissolved in chloroform and chromatographed on a silica gel column with a chloroform-ethyl acetate gradient as eluant to give the title product, 525 mg (83%).

EXAMPLE 7

Benzyl 1,2-dihydro-2-oxo-1α-(phenoxyacetylamino)-9bβH-azeto[2,1-a]isoquinoline-4-carboxylate The product of Example 6 (309 mg, 0.58 mmol) was dissolved in freshly distilled tetrahydrofuran (20 ml) and cooled to −6°. To the cold solution was added pyridine (68 μl, 0.847 mmol) and thionyl chloride (58 μl, 0.812 mmol), and the reaction was stirred for 2 hours at −6°. The solid pyridine salt was collected and the filtrate was evaporated to dryness under high vacuum. The chloro product was dissolved in freshly distilled tetrahydrofuran (15 ml) and was treated with pyridine (103 μl, 1.28 mmol) and triphenylphosphine (304 mg, 1.16 mmol). The reaction was refluxed 1.5 hours under an argon atmosphere, stirred overnight at room temperature, and then refluxed an additional 4.5 hours. The solution was decanted from a small amount of solid and evaporated to dryness. The oil was dissolved in chloroform:ethyl acetate (1:1) and chromatographed on silica gel (25 g) with chloroform:ethyl acetate (1:1) and the ethyl acetate as eluants to give the ylide product, 280 mg (62%).

The above product (277 mg, 0.357 mmol) was dissolved in 9:5 acetone:water (9 ml) which had been previously degassed with argon. The solution was cooled in an ice bath and treated with p-toluenesulfonic acid (277 mg, 1.46 mmol). The reaction was stirred at room temperature for 1.75 hours during which time the product precipitated. The solution was cooled in an ice bath and the title product was collected and washed with additional cold acetone-water solvent; 105 mg (65%), mp 136–8°.

EXAMPLE 8

1,2-Dihydro-2-oxo-1α-(phenoxyacetylamino)-9bβH-azeto[2,1-a]isoquinoline-4-carboxylic acid The product of Example 7 (55 mg, 0.12 mmol) was dissolved in freshly distilled tetrahydrofuran (24 ml) and hydrogenated at atmospheric pressure for 2 hours in the presence of 10% Pd on carbon (55 mg). The catalyst was removed by filtration and the filtrate was evaporated to dryness. The product was triturated with ether and ethyl acetate; 25 mg, mp 167–168° dec.

I claim:

1. A compound of the formula

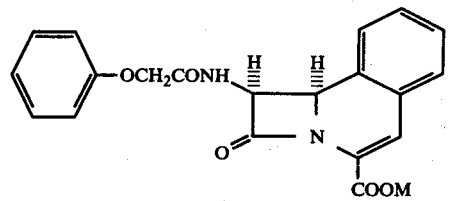

where M is hydrogen, a carboxylic acid protective ester group, or a pharmaceutically acceptable non-toxic cation.

2. A compound as claimed in claim 1 where M is hydrogen, t-butyl, benzyl, nitrobenzyl, methoxybenzyl, benzhydryl, trichloroethyl, sodium ion, or potassium ion.

3. A compound as claimed in claim 2 where M is hydrogen.

4. A compound as claimed in claim 2 where M is sodium ion.

5. A compound as claimed in claim 2 where M is potassium ion.